United States Patent [19]

Saisho et al.

[11] Patent Number: 5,414,506
[45] Date of Patent: May 9, 1995

[54] METHOD OF MEASURING REFRACTIVE INDEX OF THIN FILM AND REFRACTIVE INDEX MEASURING APPARATUS THEREFOR

[75] Inventors: Shinichiro Saisho; Toshinobu Ikeda; Akira Odagiri, all of Tokyo, Japan

[73] Assignee: Shincron Co., Ltd., Tokyo, Japan

[21] Appl. No.: 113,910

[22] Filed: Aug. 31, 1993

[30] Foreign Application Priority Data

Aug. 31, 1992 [JP] Japan .................................. 4-257463

[51] Int. Cl.⁶ ............................................. G01N 21/41
[52] U.S. Cl. ...................................... 356/128; 356/382
[58] Field of Search ................ 356/128, 382, 355, 361

[56] References Cited

U.S. PATENT DOCUMENTS 3,744,916  7/1973  Bey et al. ............................ 356/382
4,531,838  7/1983  Sawamura ........................... 356/382
4,707,611  11/1987  Southwall ........................... 356/362

*Primary Examiner*—Richard A. Rosenberger
*Attorney, Agent, or Firm*—Oblon, Spivak, McClelland, Maier, & Neustadt

[57] ABSTRACT

A method of measuring the refractive index of a thin film is composed the steps of: (a) forming a dielectric thin film which is transparent, uniform and geometrically and optically identical, on each of a first substrate and a second substrate, with the refractive indexes of the first substrate and the second substrate being different; and (b) measuring the reflectivities of the first and second substrates, each bearing the dielectric thin film thereon, with the application of a light with an identical wavelength to the two substrates, thereby measuring the refractive index of the dielectric thin film. A refractive index measuring apparatus for conducting the above method is composed of a thickness measuring optical system for sequentially guiding a luminous flux emitted from a light source to a first monitor substrate and a second monitor substrate on both of which a dielectric thin film is to be formed, and then guiding two light rays respectively reflected by the first and second monitor substrates to a light receiving unit; and an arithmetic unit for calculating the refractive index of a dielectric thin film from two intensity signals from the light receiving unit.

12 Claims, 3 Drawing Sheets

METHOD OF MEASURING REFRACTIVE INDEX OF THIN FILM AND REFRACTIVE INDEX MEASURING APPARATUS THEREFOR

BACKGROUND OF THE INVENTION

1. Field of the Invention

The present invention relates to a method of measuring the refractive index of a dielectric film and a refractive index measuring apparatus therefor, and more particularly to a method of measuring the refractive index of a dielectric thin film during the formation thereof in a thin film formation apparatus such as a vacuum deposition apparatus and a sputtering apparatus, and a refractive index measuring apparatus therefor.

2. Discussion of Background

When a thin film is formed in a vacuum thin film formation apparatus such as a vacuum deposition apparatus and a sputtering apparatus, the refractive index of a thin film formed is not necessarily the same as the refractive index of bulk material of the same composition as thin film, and usually varies depending upon the deposition conditions and other conditions in the deposition atmosphere during the formation thereof.

In particular, in the case of a reactive vacuum deposition or reactive sputtering, the above-mentioned variations in the refractive index are evident. Therefore, the variation of the refractive index of a thin film formed is inevitable even if there are slight changes in the film deposition conditions. For this reason, it is most desirable to monitor and control the deposition conditions during the formation of a thin film. Such monitoring and controlling of the film deposition conditions are extremely important particularly when optical thin films such as an anti-reflection film and a dichroic mirror are fabricated.

Furthermore, conventionally, it is impossible to measure optical constants such as the thickness of a thin film formed by vacuum deposition on the spot during the formation of the thin film, by using an optical film thickness meter, until a maximum interference value of the thin film is obtained after starting the deposition of the thin film.

Moreover, conventionally, no technique has been known for measuring the refractive index of a thin film with any thickness on the spot during the formation of the thin film. In the formation of an optical dielectric thin film, the deposited dielectric thin film exhibits a maximum value of interference for every one fourth of the wavelength ($\lambda$) of a light for measurement of the thickness, that is, $\lambda/4$. Thus, the thickness of an optical dielectric thin film is conventionally controlled during the formation thereof by utilizing this phenomenon, with a unit of $\lambda/4$. In addition, it has been reported in Japanese Laid-Open Patent Application 63-28862 that the thickness of such a thin film is controlled as desired by a certain sampling and operation.

However, in any of the above-mentioned measurement methods, the film thickness that can be measured is the optical film thickness (nd), so that it is impossible to measure optical constants of an extremely thin film, particularly on the spot during the formation thereof.

SUMMARY OF THE INVENTION

It is therefore a first object of the present invention to provide a method of measuring the refractive index of a thin film on the spot during the formation of the thin film.

A second object of the present invention is to provide a refractive index measuring apparatus for carrying out the above-mentioned refractive index measurement.

The first object of the present invention can be attained by a method comprising the steps of (a) forming a dielectric thin film which is transparent, uniform and geometrically and optically identical, on each of a first substrate and a second substrate, with the refractive indexes of the first substrate and the second substrate being different; and (b) measuring the reflectivities of the first and second substrates, each bearing the dielectric thin film thereon, with the application of a light with an identical wavelength to the two substrates, thereby measuring the refractive index of the dielectric thin film on the spot during the formation of the dielectric thin film.

The second object of the present invention can be attained by a refractive index measuring apparatus comprising a thickness measuring optical system for sequentially guiding a luminous flux emitted from a light source to a first monitor substrate and a second monitor substrate on both of which a dielectric thin film is to be formed, and then guiding two light rays respectively reflected by the first and second monitor substrates to light receiving means; and operation means for calculating the refractive index of the dielectric thin film from two intensity signals from the light receiving means.

In the above refractive index measuring apparatus, if a reference light for correcting the intensity of the light flux from the light source, and a dark light for correcting a stray light which enters the light receiving means, and also for correcting the circuits for the light receiving means are led to the light receiving means while the light reflected by the first monitor substrate and the light reflected by the second monitor substrate are sequentially measured, the refractive index of the thin film can be easily measured and controlled on the spot during the fabrication of the thin film.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
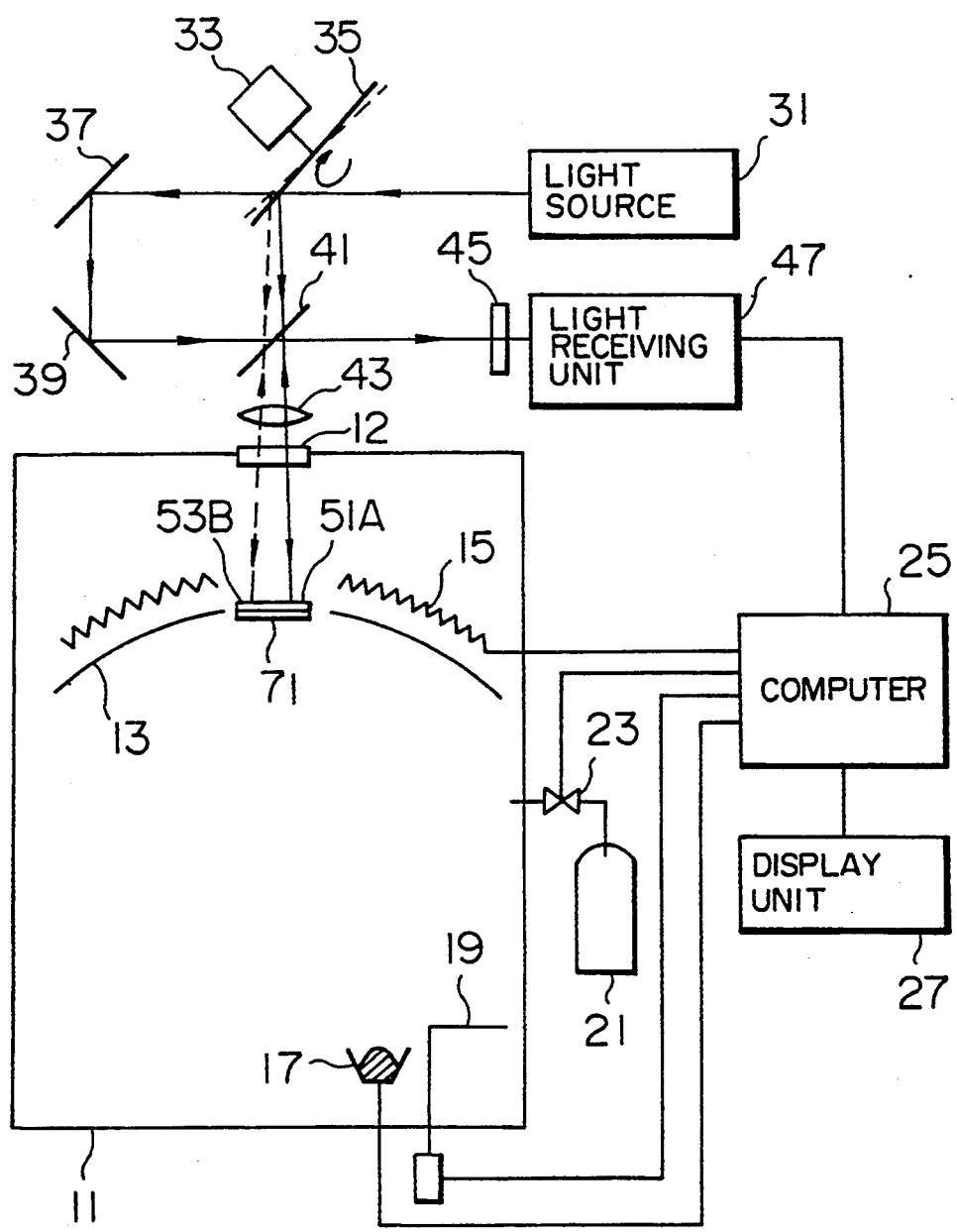
FIG. 1 is a diagram in explanation of an example of a refractive index measuring apparatus according to the present invention.

The reflectivity R of a monitor substrate on which a dielectric thin film with a refractive index n and a geometrical film thickness d is formed can be provided by the following function (1):

$$R = f(n, d, ns, \lambda) \quad (1)$$

wherein n is the refractive index of the thin film, d is the geometrical film thickness of the thin film, ns is the refractive index of the monitor substrate, and λ is the wavelength of a light for measuring the refractive index of the thin film.

When a thin film with a refractive index n and a geometrical film thickness d (i.e., a thin film with an optical film thickness nd) is provided by deposition on each of two monitor substrates with different refractive indexes, and the reflectivity $R_{g1}$ of one of the two monitor substrates and the reflectivity $R_{g2}$ of the other monitor substrate are measured by applying a light with an identical wavelength λ, the refractive index n and the geometrical film thickness d of the thin film can be obtained.

More specifically, the refractive index n and the geometrical film thickness d of the thin film can be obtained from the following Equation (2) by measuring the two reflectivities $R_{g1}$ and $R_{g2}$:

$$X = \frac{2 \cdot G_1 \cdot G_2(G_2 \cdot E_1 \cdot D_2 - G_1 \cdot D_1 \cdot E_2) + D_1 \cdot D_2(G_2^2 - G_1^2)}{2(G_1 \cdot E_1 \cdot D_2 - G_2 \cdot D_1 \cdot E_2) - D_1 \cdot D_2(G_2^2 - G_1^2)} \quad (2)$$

wherein X is $n^2$, wherein n is the refractive index of the thin film, $G_1$ is the refractive index $ns_1$ of the first substrate, $G_2$ is the refractive index $ns_2$ of the second substrate, $R_{g1}$ is the refractivity of the first substrate when a thin film with an optical film thickness nd is deposited thereon, $R_{g2}$ is the refractivity of the second substrate when a thin film with an optical film thickness nd is deposited thereon, $D_1$ is $R_{g1}-1$, $E_1$ is $R_{g1}+1$, $D_2$ is $R_{g2}-1$, $E_2$ is $R_{g2}+1$.

It is necessary that the reflectivity $R_{g1}$ and the reflectivity $R_{g2}$ be respectively determined as an absolute intensity in the form of a ratio of incident light intensity/reflected light intensity. In order to do this, it is necessary to use a reference substrate with a known refractive index, which is chemically stable, such as a quartz substrate, and to obtain the correlation between the reflected light quantity and the reflectivity thereof to be measured.

In the above method, a dielectric thin film is deposited, for instance, by vacuum deposition, on the surface of each of two transparent substrates made of an optical glass with a known refractive index serving as the first and second monitor substrates, so that the reflectivity of the back side of each substrate can be measured during the formation of the dielectric thin film by vacuum deposition. Thus, a thin film with a predetermined refractive index can be formed by controlling the conditions for the film formation, such as the deposition (sputtering) rate, the temperature of the substrates, and partial gas pressures in the atmosphere for the deposition (in the case of reactive deposition, and reactive sputtering), so as to make up for the deviation of the predetermined value of the refractive index.

The calculation of the refractive index of a thin film by use of the previously mentioned Equation (2) will now be explained more specifically.

When an incident light with a wavelength λ is caused to perpendicularly strike a non-light-absorbing, uniform, thin film, which has a refractive index n and a geometrical film thickness d, and is deposited on a transparent substrate with a refractive index ns, the optical characteristics of the substrate deposited with the thin film are shown by the following matrix:

$$M = \begin{bmatrix} \cos\delta & (i/n)\sin\delta \\ in\sin\delta & \cos\delta \end{bmatrix}$$

wherein $$\delta = \frac{2\pi nd}{\lambda}$$

The energy reflectivity R is shown by the following Function (3):

$$R = \frac{[(1 - ns)\cos\delta]^2 + [\{(ns/n) - n\}\sin\delta]^2}{[(1 + ns)\cos\delta]^2 + [\{(ns/n) + n\}\sin\delta]^2}$$

Function (3) can also be represented as follows:

$$R = f(n, d, ns, \lambda)$$

When the wavelength λ, and the refractive index ns of the transparent substrate are known, the refractive index n and the geometrical film thickness d of the deposited thin film can be calculated by solving simultaneous quadratic equations.

When two substrates with different refractive indexes $ns_1$ and $ns_2$ are prepared, functions $R_1$ and $R_2$ are as follows:

$$R_1 = f(n, d, ns_1, \lambda) \quad (4\text{-}1)$$

$$R_2 = f(n, d, ns_2, \lambda) \quad (4\text{-}2)$$

The above Functions (4-1) and (4-2) can be respectively rewritten as follows by using the previously mentioned Equation (3):

$$R_1 = \frac{X(1 - Y)(1 - ns_1)^2 + Y(ns_1 - X)^2}{X(1 - Y)(1 + ns_1)^2 + Y(ns_1 + X)^2} \quad (5\text{-}1)$$

$$R_2 = \frac{X(1 - Y)(1 - ns_2)^2 + Y(ns_2 - X)^2}{X(1 - Y)(1 + ns_2)^2 + Y(ns_2 + X)^2} \quad (5\text{-}2)$$

wherein $X = n^2$, and $Y = \sin^2\delta$

When Equations (5-1) and (5-2) are solved with respect to X, Equation (3) can be derived.

FIG. 1 is a diagram in explanation of an example of a refractive index measuring apparatus according to the present invention. In a vacuum chamber 11 of this refractive index measuring apparatus, there are provided a deposition source 17, a shutter 19 for controlling the ejection of a deposition material to be deposited from the deposition source 17, a substrate holder 13 for holding a substrate onto which the deposition material is to be deposited, and a heater 15 for heating the substrate. Furthermore, there is provided a monitor glass, which is composed of a monitor glass substrate 51A and a monitor glass substrate 53B for monitoring the refractive index and thickness of a thin film to be formed on the substrate by vacuum deposition.

Figure 3:
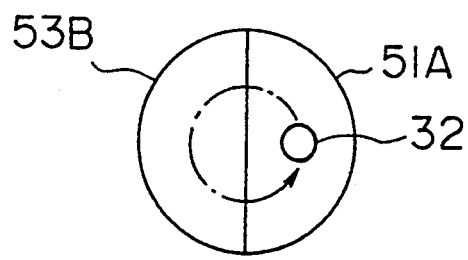
FIG. 3 is a plan view of an example of a monitor glass substrate, with an illustration of a locus of a light spot.

FIG. 3 is a plan view of the monitor glass substrate which is composed of the monitor glass substrate 51A and the monitor glass substrate 53B. The refractive indexes of the two monitor glass substrates 51A and 53B are different.

The vacuum chamber 11 is also provided with a gas cylinder 21 for introducing a gas such as oxygen into the vacuum chamber 11, a variable valve 23 for controlling the amount of the gas to be introduced into the vacuum chamber 11, and a transparent monitoring window 12 made of a glass.

The refractive index measuring apparatus of the present invention comprises a computer 25, a light source 31, a scanning motor 33, a scanning mirror 35, a high reflection mirror section 35A, a high reflection mirror section 35B, a cut-away section 35C, an opaque, non-reflecting section 35D, mirrors 37 and 39, a half-mirror 41, a lens 43, a narrow band interference filter 45 and a light receiving unit 47. In this refractive index measuring apparatus, a collimator luminous flux emitted from the light source 31 is reflected by the scanning mirror 35, passes through the half-mirror 41, the lens 43, and the monitoring window 12, and projected in the shape of a spot on the monitor glass substrate 51A or 53B. The light is then reflected by the monitor glass substrate 51A or 53B, passes through the monitoring window 12 and the lens 43, and is then reflected by the half-mirror 41. The light reflected by the half-mirror 41 is then led to a light receiving unit 47 through the interference filter 45 with a transmission center wavelength λ, so that the intensity of the reflected light is measured.

Depending upon a rotated posture of the scanning mirror 35, the luminous flux from the light source 31 passes through the scanning mirror 35 and directly enters the light receiving unit 47 through mirrors 37, 39 and the half-mirror 41. The wavelength λ of the light for the measurement of the light can be set as desired by the interference filter 45.

Figure 2:
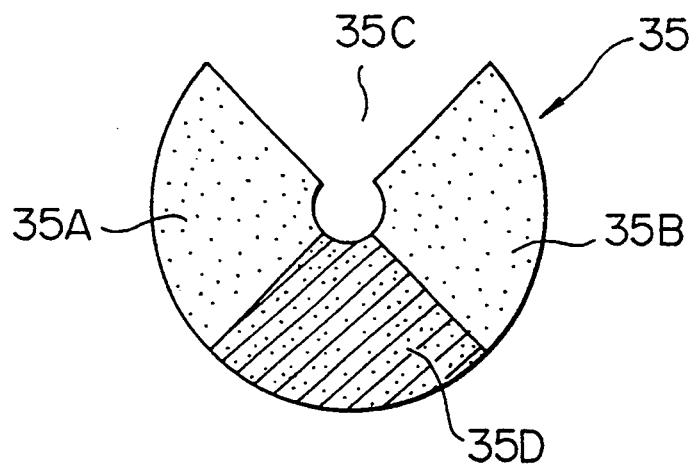
FIG. 2 is a plan view of a scanning mirror for use in the present invention.

The scanning mirror 35 is segmented into four zones as illustrated in a plan view thereof in FIG. 2. More specifically, the scanning mirror 35 is composed of high reflection mirror sections 35A and 35B with an aluminum film deposited thereon, an opaque, non-reflecting section 35D which minimizes the reflection and transmission of the luminous flux emitted from the light source 31, for instance, by applying thereto a back coating, and a cut-away section 35C, which is cut away from the scanning mirror 35 in order to prevent any and all reflection by the scanning mirror 35.

The reflection characteristics of the high reflection mirror sections 35A and 35B are made identical. In place of the cut-away section 35C, a transparent section without any deposition thereon or with an antireflection film can be formed in the scanning mirror 35.

The scanning mirror 35 is fixed to a rotary shaft of a scanning motor 33, with an angle deviating from a right angle to the rotary shaft. Thus, as shown by the solid line and the broken line in FIG. 1, the angle between the scanning mirror 35 and the luminous flux emitted from the light source 31 varies during the rotation of the scanning mirror 35, so that a light spot 32 formed on the monitor glass substrates 51A and 53B by the light reflected from the scanning mirror 35 makes a circular motion as shown by the arrow in FIG. 3. More specifically, the luminous flux reflected by the high reflection mirror section 35A of the rotating scanning mirror 35 is projected on the monitor glass substrate 51A, while the luminous flux reflected by the high reflection mirror section 35B is projected on the monitor glass 53B. The monitor glass substrates 51A and 53B are stationary.

Figure 4:
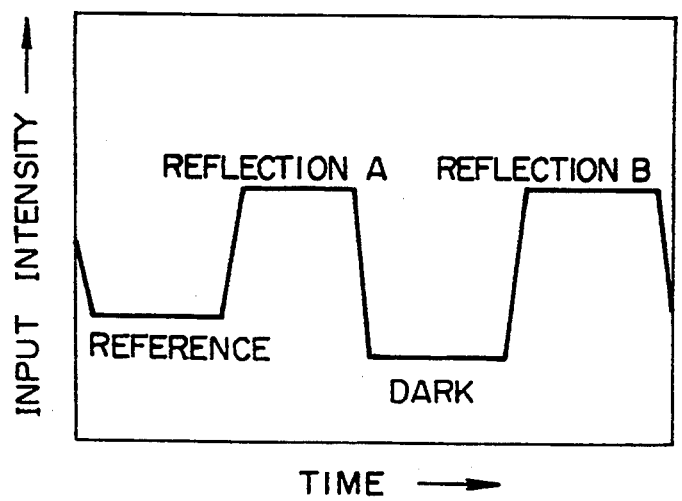
FIG. 4 is a graph showing an input state of a reflection signal light.

Therefore, as shown in FIG. 4, in synchronization with the rotation of the scanning mirror 35, signals are input to the light receiving unit 47 in the order of (a) reference (a luminous flux passed through the cut-away portion 35C), (b) reflection A (reflection light from the monitor glass 51A), (c) dark (light which is inevitably reflected by the opaque, non-reflecting section 35D, and reflected by an intermediate area between the monitor glass substrate 51A and the monitor glass substrate 53B, which is an extremely slight reflection light, ideally with a zero input signal), and (d) reflection B (reflection light from the monitor glass 53B).

The intensity of the reference is determined depending upon the reflectivities of the mirrors 37 and 39, and the transmittance of the half-mirror 41. Therefore, the reference can be used as a reference light with a fixed intensity for correcting the intensity of the light from the light source 31. Furthermore, the reference can be used as a signal light for distinguishing between the reflection A and the reflection B.

The dark with a substantially zero input signal can be used to correct the stray light and the circuits of the light receiving unit. The dark is also used as a signal light for distinguishing between the reflection A and the reflection B.

When a dielectric thin film 71 is provided by deposition on the transparent monitor glass substrates 51A and 53B, the reflectivities of the monitor glass substrates 51A and 53B change because the refractive indexes of the monitor glass substrates 51A and 53B are different, so that the input intensities of the reflection A and the reflection B are changed. The nd of the formed dielectric thin film 71, in which n is the refractive index, and d is the geometrical thickness), is the same in the two monitor glass substrates 51A and 53B. Therefore, as mentioned previously, by measuring the reflection intensities of the reflection A and the reflection B, the refractive index n of the dielectric thin film can be calculated on the spot by a computer 25 (arithmetic unit), and the calculated refractive index n can be displayed on a display unit 27.

When the refractive index is to be determined, it is necessary to obtain the absolute values (not relative values) of the reflectivities of the monitor glass substrates 51A and 53B. In order to do this, it is necessary to set up a measurement system provided with a chemically stable reference substrate, with the refractive index thereof at the wavelength of the light for the measurement being known. In the present invention, a quartz substrate is used as such a reference substrate, since it is the most stable substrate. In order to establish the correlation between electrical signals from the light receiving unit and the quantity of the reflection light input thereto, the reflectivity of the quartz substrate is calculated based on the refractive index of the quartz substrate, so that the correlation between the quantity of the reflection light and the reflectivity of the quartz substrate in this optical system can be established. Thus, the reflectivity of each monitor substrate is determined as the absolute intensity.

When the refractive index n of the dielectric thin film 71 formed by deposition varies, the deposition conditions of the deposition source 17, the substrate heating conditions by the heater 15, the gas introducing conditions by the variable valve 23 are adjusted in accordance with the properties of the deposited material for the dielectric thin film 71, and when the above conditions exceed the respective predetermined ranges, the deposition is stopped by closing a shutter 19.

Figure 5:
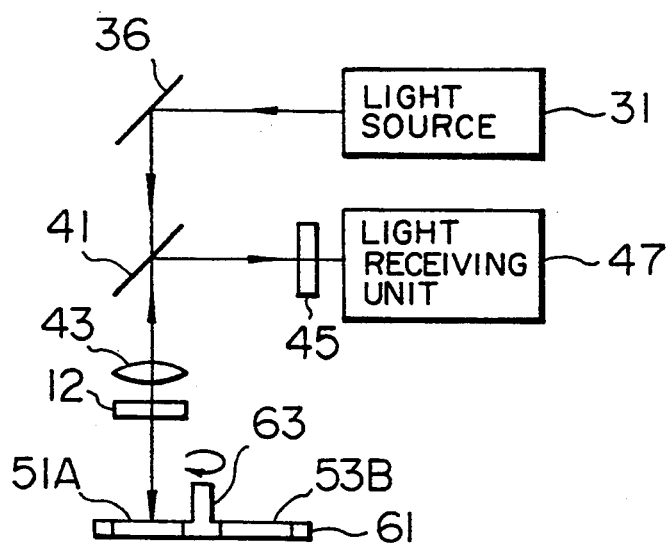
FIG. 5 is a partial diagram in explanation of another example of a refractive index measuring apparatus according to the present invention.

FIG. 5 is a diagram in explanation of another example of a refractive index measuring apparatus according to the present invention, in which like reference numerals designate identical or substantially identically modified parts to FIG. 1.

Figure 6:
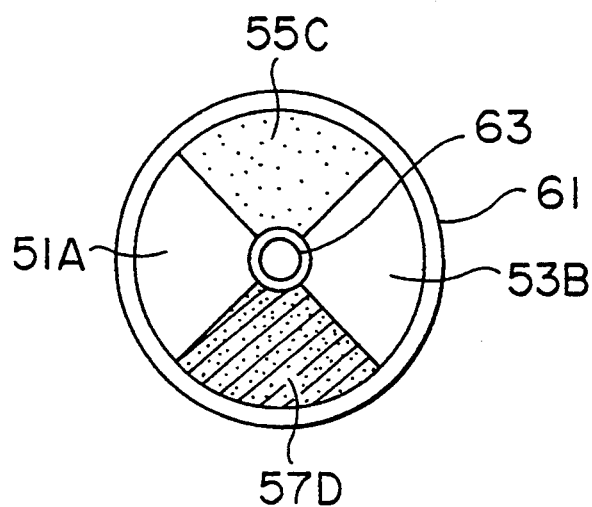
FIG. 6 is a plan view of another example of a monitor glass substrate for use in the present invention.

FIG. 6 is a plan view of a monitor glass substrate with a holder 61 therefor.

A parallel luminous flux emitted from a light source 31 is projected in the form of a light spot onto a monitor glass substrate 51A through a mirror 36, a half-mirror 41, a lens 43, and a monitoring window 12. The light reflected from the monitor glass substrate 51A is returned through the same path as mentioned above and is then reflected by the half mirror 41 and enters a light receiving unit 47 through an interference filter 45.

In the monitor glass substrate holder 61, there are incorporated two monitor glass substrates 51A and 53B with different refractive indexes, an opaque reflection mirror 55C provided with a mirror film at an upper surface thereof (refer to FIG. 5), and an opaque, non-reflecting board 57D. By rotating the monitor glass substrate holder 61 through a driving shaft 63, the light from the light source 31 is sequentially reflected by the reflection mirror 55C, the monitor glass substrate 51A, the opaque non-reflecting board 57D, and the monitor glass substrate 53B. The reflectivities of the reflection mirror 55C and the opaque, non-reflecting board 57D are not changed by the formation of the thin film, so that the reflection light from the reflection mirror 55C can be used as the reference shown in FIG. 4, and the light signal at the incidence of the light on the opaque, non-reflecting board 57D can be used as the dark.

On the other hand, the reflectivities of the monitor glass substrates 51A and 53B With different refractive indexes are changed by the formation of the thin film, so that the refractive index n of the formed dielectric thin film can be measured by utilizing the respective signals of the reflection A and reflection B as shown in FIG. 4.

According to the present invention, the refractive index n of a thin film can be measured. In particular, the refractive index of a thin film which is being formed by a film formation method such as vacuum deposition or sputtering can be measured on the spot during the formation of the thin film, so that the conditions for the formation of the thin film can be easily monitored and controlled.

What is claimed is:

1. A method of measuring the refractive index of a dielectric thin film, comprising the steps of:
   (a) forming a dielectric thin film which is transparent, uniform, and geometrically and optically identical, on each of a first substrate and a second substrate, with refractive indexes of said first substrate and said second substrate being different from one another; and
   (b) measuring the reflectivities of said first and second substrates, each bearing said dielectric thin film thereon, with the application of a light with an identical wavelength to said two substrates; and
   (c) calculating the refractive index of the dielectric thin film using the measured reflectivities of said first and second substrates.

2. The method of measuring the refractive index of a dielectric thin film as claimed in claim 1, wherein the step of calculating the refractive index of the dielectric thin film comprises solving the following equation for X:

$$X = \frac{(2G_1G_2(G_2E_1D_2 - G_1D_1E_2) + D_1D_2(G_2^2 - G_1^2)}{2(G_1E_1D_2 - G_2D_1E_2) - D_1D_2(G_2^2 - G_1^2)}$$

wherein X is $n^2$, n is the refractive index of said dielectric thin film, $G_1$ is the refractive index $ns_1$ of said first substrate, $G_2$ is the refractive index $ns_2$ of said second substrate, $Rg_1$ is the refractivity of said first substrate when a thin film with an optical film thickness nd is deposited thereon, $Rg_2$ is the refractivity of said second substrate when a thin film with an optical film thickness nd is deposited thereon, $D_1$ is $Rg_1-1$, $E_1$ is $Rg_1+1$, $D_2$ is $Rg_2-1$, and $E_2$ is $Rg_2+1$.

3. The method of measuring the refractive index of a thin film as claimed in claim 1 or claim 2, wherein the refractive index of said dielectric thin film is measured on the spot during the formation of said dielectric thin film.

4. A refractive index measuring apparatus, comprising:
   a light source for generating a luminous flux;
   light receiving means for receiving light and determining intensity of luminous flux of the received light;
   a first monitor substrate having a first index of refraction;
   a second monitor substrate having a second index of refraction that is different from said first index of refraction, wherein a dielectric film is to be formed on both the first and second monitor substrates;
   a thickness measuring optical system comprising
   (a) means for sequentially guiding said luminous flux emitted from said light source to said first monitor substrate and to said second monitor substrate, and
   (b) means for guiding first and second light rays which are, respectively, reflections by said first and second monitor substrates of the sequentially guided luminous flux, to said light receiving means, wherein said light receiving means determines first and second intensity signals from said first and second light rays, respectively; and
   operation means, coupled to said light receiving means, for calculating the refractive index of said dielectric thin film from said first and second intensity signals.

5. An apparatus according to claim 4, wherein said means for sequentially guiding further comprises means for sequentially guiding said luminous flux from said light source to said light receiving means, wherein said luminous flux bypasses said first monitor substrate and said second monitor substrate; and said thickness measuring optical system further comprising:
   (d) means for preventing the luminous flux generated by the light source from reaching the light receiving means, so that the intensity of stray light being received by the light receiving means can be measured.

6. An apparatus according to claim 4, wherein said means for sequentially guiding comprises a scanning mirror.

7. An apparatus according to claim 4, wherein said means for sequentially guiding comprises a scanning mirror and a means for rotating the scanning mirror.

8. An apparatus according to claim 4, wherein said means for sequentially guiding comprises a scanning mirror and a means for rotating the scanning mirror, and wherein said scanning mirror comprises a first reflective surface and a second reflective surface and the first and second reflective surfaces are not parallel.

9. An apparatus according to claim 4, wherein:
the first and monitor substrate has first and second major surfaces,
the second monitor substrate has first and second major surfaces, and
further comprising a means for depositing the dielectric film on the first major surfaces of the first and second monitor substrates,
wherein said means for sequentially guiding guides said luminous flux toward said second major surfaces of said first and second monitor substrates.

10. An apparatus according to claim 4, wherein said operation means for calculating the refractive index of said dielectric thin film comprises means for solving the following equation for X:

$$X = \frac{(2G_1G_2(G_2E_1D_2 - G_1D_1E_2) + D_1D_2(G_2^2 - G_1^2)}{2(G_1E_1D_2 - G_2D_1E_2) - D_1D_2(G_2^2 - G_1^2)}$$

wherein X is $n^2$ wherein n is the refractive index of said dielectric thin film, $G_1$ is the refractive index $ns_1$ of said first substrate, $G_2$ is the refractive index $ns_2$ of said second substrate, $Rg_1$ is the refractivity of said first substrate when a thin film with an optical film thickness nd is deposited thereon, $Rg_2$ is the refractivity of said second substrate when a thin film with an optical film thickness nd is deposited thereon, $D_1$ is $Rg_1-1$, $E_1$ is $Rg_1+1$, $D_2$ is $Rg_2-1$, and $E_2$ is $Rg_2+1$.

11. An apparatus according to claim 4, wherein said light source emits the same frequency of light during sequential guiding of luminous flux to said first and second monitor substrates.

12. An apparatus according to claim 4, wherein the apparatus is configured so that the dielectric film to be formed on both the first and second monitor substrates has the same thickness on both the first and second monitor substrates.

* * * * *

UNITED STATES PATENT AND TRADEMARK OFFICE
CERTIFICATE OF CORRECTION

PATENT NO. : 5,414,506
DATED : MAY 9, 1995
INVENTOR(S) : Shinichiro SAISHO ET AL It is certified that error appears in the above-indentified patent and that said Letters Patent is hereby corrected as shown below:

IN THE CLAIMS

Column 8, line 6, delete "(" (first occurrence).

Column 10, line 2, delete "(" (first occurrence).

Signed and Sealed this

Second Day of April, 1996

Attest:

BRUCE LEHMAN

Attesting Officer     Commissioner of Patents and Trademarks